(12) United States Patent
Tillmans

(10) Patent No.: US 6,322,614 B1
(45) Date of Patent: Nov. 27, 2001

(54) DEVICE FOR HIGH-PURITY FILTERING AND DISINFECTING BREATHING AIR

(76) Inventor: Kurt Tillmans, Triererstrasse 301, D56072 Koblenz (DE)

(*) Notice: Subject to any disclaimer, the term of this patent is extended or adjusted under 35 U.S.C. 154(b) by 0 days.

(21) Appl. No.: 09/202,222
(22) PCT Filed: Jun. 20, 1997
(86) PCT No.: PCT/DE97/01283
§ 371 Date: Dec. 9, 1998
§ 102(e) Date: Dec. 9, 1998
(87) PCT Pub. No.: WO98/26810
PCT Pub. Date: Jun. 25, 1998

(30) Foreign Application Priority Data

Dec. 18, 1996 (DE) .............................. 196 52 688

(51) Int. Cl.⁷ .................................................. B03C 3/016
(52) U.S. Cl. .................................. 96/16; 55/487; 95/287; 95/901; 96/63; 96/224
(58) Field of Search .................................. 55/385.1, 485, 55/486, 487; 96/16, 223, 224, FOR 175, 63; 95/286, 287, 901; 422/24, 121

(56) References Cited

U.S. PATENT DOCUMENTS

| | | |
|---|---|---|
| 2,500,007 | 3/1950 | Polevitsky . |
| 3,239,305 | 3/1966 | Potapenko . |
| 3,967,927 | 7/1976 | Patterson . |

(List continued on next page.)

FOREIGN PATENT DOCUMENTS

| | | |
|---|---|---|
| 14 54 637 | 3/1969 | (DE) . |
| 20 35 789 | 2/1971 | (DE) . |
| 722 14 61 | 5/1972 | (DE) . |
| 20 63 762 | 6/1972 | (DE) . |
| 21 25 206 | 11/1972 | (DE) . |
| 23 24 881 A1 | 12/1974 | (DE) . |
| 33 31 864 A1 | 3/1985 | (DE) . |
| 34 05 142 A1 | 9/1985 | (DE) . |
| 35 17 105 C1 | 11/1985 | (DE) . |
| 21 64 140A | 3/1986 | (DE) . |
| 35 01 678 A1 | 7/1986 | (DE) . |
| 30 03 413 C2 | 1/1987 | (DE) . |
| 36 18 499 A1 | 12/1987 | (DE) . |
| 36 32 372 A1 | 3/1988 | (DE) . |
| 36 40 743 A1 | 6/1988 | (DE) . |
| 37 03 137 A1 | 8/1988 | (DE) . |
| 37 35 251 A1 | 4/1989 | (DE) . |
| 38 03 613 C2 | 8/1990 | (DE) . |
| 93 01 714 U1 | 5/1993 | (DE) . |
| 42 10 509 A1 | 10/1993 | (DE) . |
| 93 13 409 | 11/1993 | (DE) . |

(List continued on next page.)

OTHER PUBLICATIONS

Hillebracht, Juergen, Kohler, Miklaus: UV–C–Luftenkeimung in Klimaanlagen. In: Ki Klima, Kaelte, Heizung Feb. 1989, S.65–68.

Neuman, Wolfhart: Luftfiltertechnik. In: IKZ–Haustechnik, H.7, 1995, S. 104–110.

Biehler, M.J., Buchholz, R.: Abscheideleistung von Filtern in Lueftungsanlagen. In: TAB 12/96, S.41–46.

Primary Examiner—Richard L. Chiesa
(74) Attorney, Agent, or Firm—Flynn, Thiel, Boutell & Tanis, P.C.

(57) ABSTRACT

The present invention refers to a device for high-purity filtering and disinfecting breathing air. The device includes a fine-dust filter and fan arranged on a housing. An elongate air flow tube is also arranged on the housing and is oriented to receive air flow from the housing. A second filter for disinfecting air is included in the elongate air flow tube. Arranged in series in the air flow tube are a third, main filter for removing microorganisms and a fourth, activated carbon filter for removing noxious fumes.

14 Claims, 3 Drawing Sheets

U.S. PATENT DOCUMENTS

| | | | | |
|---|---|---|---|---|
| 4,210,429 | * | 7/1980 | Golstein | 96/224 X |
| 4,344,776 | * | 8/1982 | Yavnieli | 96/63 |
| 5,225,167 | * | 7/1993 | Wetzel | 96/224 |
| 5,240,478 | * | 8/1993 | Messina | 96/224 X |
| 5,399,319 | * | 3/1995 | Schoenberger et al. | 96/224 |
| 5,523,057 | * | 6/1996 | Mazzilli | 96/224 |
| 5,558,158 | | 9/1996 | Elmore . | |
| 5,603,562 | | 2/1997 | Huang . | |
| 5,616,172 | * | 4/1997 | Tuckerman et al. | 96/224 |
| 5,654,242 | * | 8/1997 | Morrow et al. | 96/224 |
| 5,779,769 | * | 7/1998 | Jiang | 96/16 |
| 5,837,207 | * | 11/1998 | Summers | 96/224 |

FOREIGN PATENT DOCUMENTS

| | | |
|---|---|---|
| 93 16 234 U1 | 2/1994 | (DE) . |
| 44 09 806 A1 | 9/1995 | (DE) . |
| 44 30 231 A1 | 2/1996 | (DE) . |
| 195 30 785 C1 | 11/1996 | (DE) . |
| 296 22 001 | 4/1997 | (DE) . |
| 0 461 310 | 12/1991 | (EP) . |
| 1 400 519 | 7/1975 | (GB) . |
| WO95/17634 | 6/1995 | (WO) . |
| WO95/35123 | 12/1995 | (WO) . |
| WO95/35123 A1 | 12/1995 | (WO) . |

* cited by examiner

DEVICE FOR HIGH-PURITY FILTERING AND DISINFECTING BREATHING AIR

CROSS-REFERENCE TO RELATED APPLICATION

This application is a national stage application corresponding to International Application No. PCT/DE97/01283, filed Jun. 20, 1997.

FIELD OF THE INVENTION

The present invention refers to a method and a device for high-purity filtering and disinfecting breathing air.

The present invention also refers to a floor lamp provided with such a device.

BACKGROUND OF THE INVENTION

The air contains a large number of contaminations which can cause great damage in the field of industry. In archives, for example, the drawings stored on safety films can get lost if said safety films are attacked by microorganisms.

Contaminations contained in the breathing air can cause essential damage as well. Due to bacteria, viruses and mould fungi, employees may, for example, fall ill whose sick pay can cost a substantial amount of money.

Furthermore, pollen often cause irritations of the mucosa resulting in serious indisposition.

Suspended particulates or microorganisms can especially also impair the healing process of human beings with a reduced power of resistance, like those affected by hepatitis C or immuno-deficiencies, furthermore dialysis patients, allergic persons, asthmatics and patients who are affected by neuro-dermatitis.

In the Federal Republic of Germany alone, the health and well-being of 30 million human beings is impaired by contaminations in the breathing air.

In order to enable allergic persons to prepare themselves for the often serious disturbances of health, information indicating the kind of pollen that has to be reckoned with is included in the weather report at the relevant times.

Also in sick-rooms and nurseries, bacteria, viruses and mould fungi can be very injurious to health.

Lying down e.g. in a sick-room, an adult breathes in approx. 5 liters of air in one minute.

Standing still, he breathes in approx. 8 liters of air per minute.

During a slow walk, the amount of breathing air increases to 17 liters.

When he engages in sporting activities, e.g. competitive rowing, an adult will breath in up to 140 liters in one minute.

Indoors, the amount of air consumed can be assumed to be approx. 12 liters per minute.

In waiting rooms, offices, restaurants, aeroplanes, an exchange of air is often not provided; in some cases, only a small amount of fresh air of the air conditioning system is supplied so that all the viruses and bacteria spread everywhere.

Contaminations of the breathing air can be subsumed in three groups:

1. Contaminations caused by suspended particulates
   a) house dust
   b) mites
   c) skin scales
   d) soot
   e) pollen
   f) other organic contaminations
2. Contaminations caused by microorganisms
   g) bacteria
   h) viruses
   i) mould fungi
3. Contaminations in the form of gases
   j) formaldehyde
   k) carbon monooxide
   l) noxious fumes
   m) unpleasant smells, e.g. cigarette smoke It is the object of the present invention to subject air, especially breathing air, to high-purity filtering and to disinfect it.

SUMMARY OF THE INVENTION

According to the present invention, this object is achieved by the features that
   a) the air is conducted through a roughing filter,
   b) the air is irradiated with UV-C light,
   c) the air is conducted through a main filter and
   d) the air flows through an active carbon filter.

BRIEF DESCRIPTION OF THE DRAWINGS

The present invention is explained in detail on the basis of three embodiments.

In the drawings.

DETAILED DESCRIPTION

Figure 1:
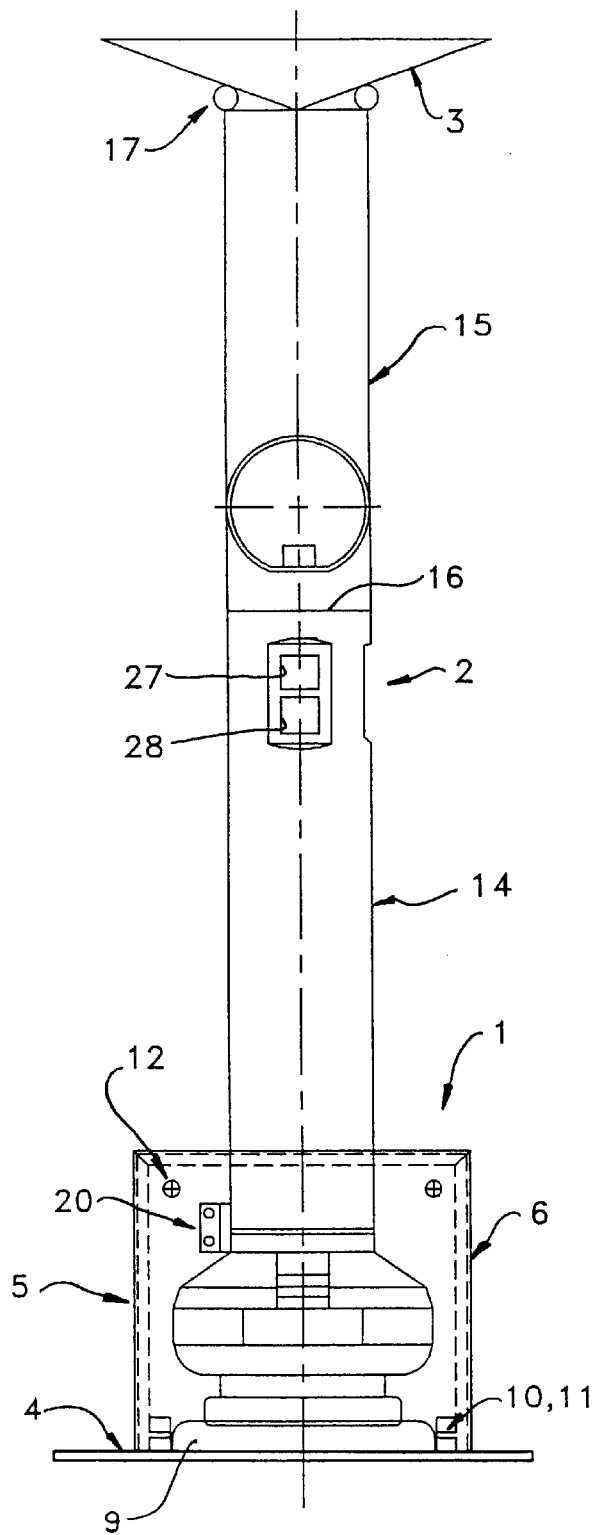
FIG. 1 shows a front view of a first embodiment of the high-purity filtering and disinfecting device according to the present invention.
Figure 2:
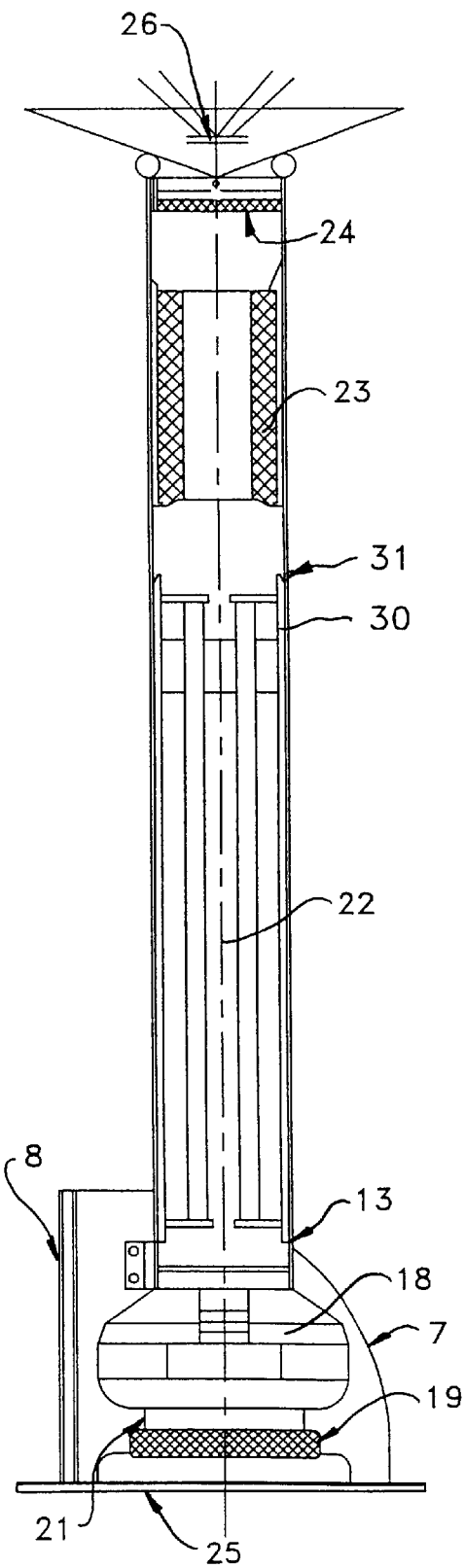
FIG. 2 shows a vertical section.

FIGS. 1 and 2 show a first embodiment of a device according to the present invention. Externally, the device can be divided into three areas:
   a lower area, the housing 1, a central area, the tube 2, and an upper area, the discharge cone 3.

The sheet-metal housing 1 comprises a flat base plate 4, the flat side walls 5, 6, a curved front wall 7 and a removable rear wall 8. The side walls 5, 6 and the front wall 7 are secured to the base plate 4. Preferably, fastening is effected by means of a welded joint. In addition, the side walls 5, 6 and the front wall 7 are also welded together at the abutting edges.

The side walls 5, 6 and the front wall 7 have openings 9 in their areas facing the base plate 4. These openings 9 serve to suck in the ground air.

The rear wall 8 is secured in position such that it is easily removable. In the lower area it is held in two openings 10 by means of sheet-metal tongues 11, and in the upper area it is held by two screws 12.

The front wall 7 has in the upper area thereof an opening 13 through which the tube 2 is introduced in the sheet-metal housing 1. The tube 2 is welded to the edge of the opening 13.

The tube 2 consists of a lower tubular component 14 and of an upper tubular component 15. The two tubular components 14/15 are fitted together. Reference numeral 16 designates the parting plane of the tubular components 14, 15.

The lower tubular component 14, which is welded to the housing 1, has a uniform diameter up to the parting plane 16. From the parting plane 16 onwards, the outer diameter is reduced in size. The tubular component 14 slightly projects beyond the parting plane with a reduced external diameter.

The upper tubular component 15 has a reduced internal diameter in the area of the parting plane 16 in such a way that the two tubular components can easily be fitted together. Instead of machining the diameters of the tubes, it is also possible to weld an additional tubular member into the tubular component 14, the external diameter of said additional tubular member corresponding approximately to the internal diameter of the tubular components 14, 15. The part projecting beyond the tubular component 14 will then be used as a reception means for the tubular component 15.

The upper area, viz. the discharge cone 3, is connected to the tubular component 15 via a plurality of balls 17 which are uniformly distributed over the rim of the tube 2.

With regard to the structural design in the interior of the combination:

The housing 1 has provided therein a fan 18 and a fine-dust filter 19. The fan 13, preferably a fan in a tube, is fastened to the end of the tubular component 14 projecting into the housing 1, said fastening being carried out by means of a hose clamp 20 lined with insulating material. This fastening mode serves to avoid the transmission of vibrations of the fan to the tube 2 as far as possible.

On the side of the fan 18 facing the base plate 4, a housing 21 is secured in position, said housing 21 accommodating the fine-dust filter 19.

The housing 21 comprises a tubular section which is connected to the tubular outlet piece of the fan 18 in a soundproof manner. The tubular section is followed by a flat plate provided with U-shaped rails at two opposite sides thereof. The fine-dust filter 19 is inserted into said U-shaped rails. By means of thumb screws, the fine-dust filter is pressed onto the flat plate via sealing rubber strips.

The fine-dust filter 19 serves as a roughing filter. It belongs to class F6.

In the interior of the tube 2, the UV-C lamps 22, the main filter 23 and an active or activated carbon filter 24 are provided. The main filter belongs to class EU 13/14 S of the European standard. This class of high efficiency filters comprises the purest filters existing at present. They filter out bodies having a size of 1/300 000 mm.

The UV-C lamps 22 are preferably arranged in the lower area of the tube 2, in particular the lamp bases are secured in position in the lower tubular component 14.

The main filter 23 can be secured in position in the upper half of the tube by means of a screwed connection.

Mode of Operation

The ground air 25 sucked in by the fan 18 through the openings 9 flows through the fine-dust filter 19. In this fine-dust filter the contaminations of the first group, viz. the suspended particulates, are filtered out. Due to the fact that the suspended particulates are filtered out, the UV-C lamps cannot become clouded, their ability to emit rays will be preserved for a long period of time, approx. 8000 hours.

In the next step, the breathing air is conducted through the tube past the UV-C lamps. Most of the bacteria, viruses and microorganisms are destroyed by the UV-C light.

In the third step, the prefiltered and now disinfected breathing air is conducted through the main filter—an absolute filter.

The destroyed bacteria, viruses and microorganisms are here filtered out.

In the last step, the breathing air is additionally conducted through an agglomerated active carbon filter. This filter is used for the purpose of purifying the breathing air from noxious fumes (i.e., ozone) and unpleasant smells.

The resultant filtered breathing air flows at the upper end of the tube through the free space between the balls 17 and against the discharge cone 3. By means of said discharge cone, the breathing air is uniformly distributed.

Figure 3:
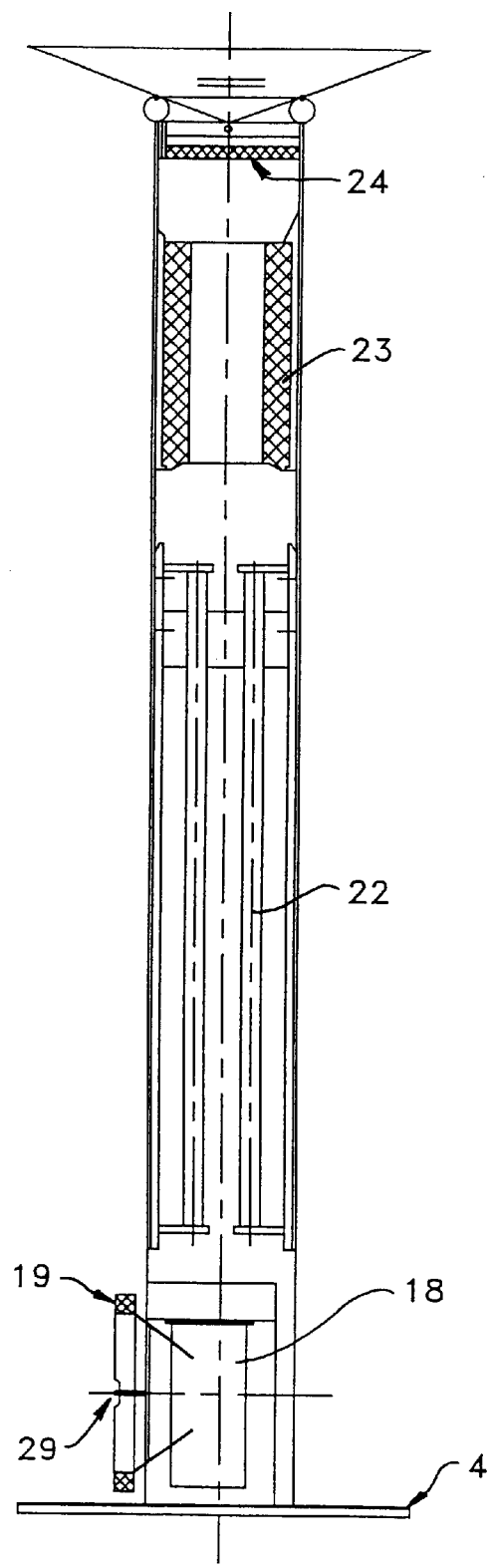
FIG. 3 shows the vertical section of a second embodiment.
Figure 4:
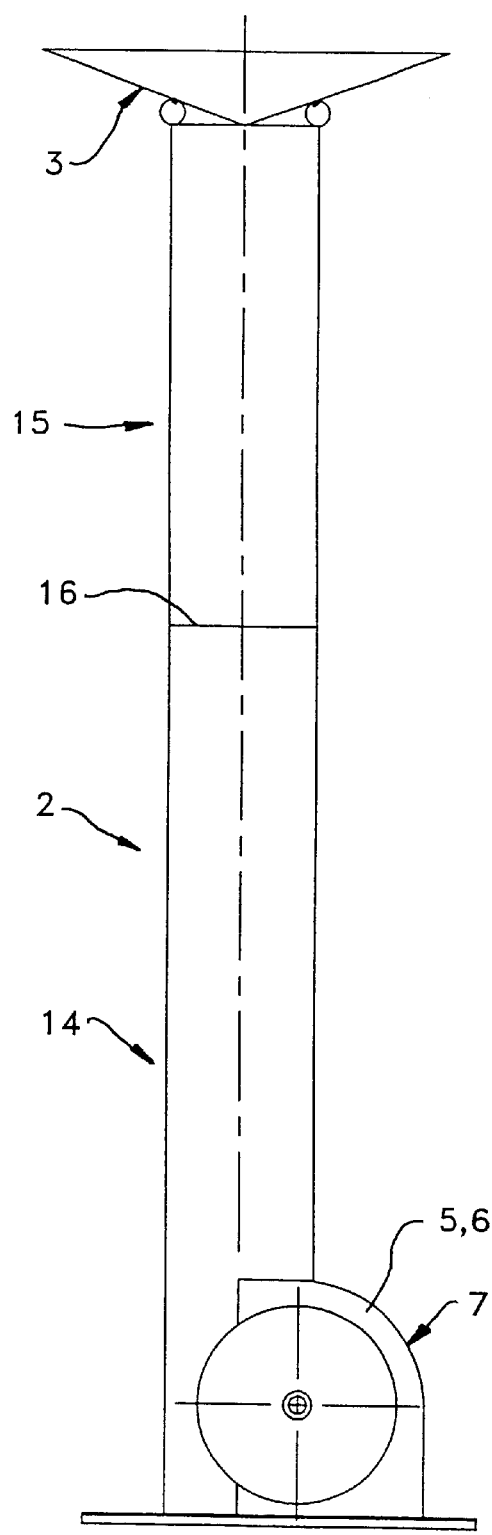
FIG. 4 shows the side view of the second embodiment.

FIGS. 3 and 4 show the second embodiment. It differs from the first one with regard to the arrangement of the fine-dust filter 19 and the fan 18.

Whereas the rear wall 8 was removable in the first embodiment so that the fine-dust filter 19 could be exchanged, the fine-dust filter 19 is arranged outside of the housing 1 in the second embodiment.

It suffices to loosen the screw 29 for removing the fine-dust filter. In the embodiment according to FIG. 2, the fan 18 was an axial-flow blower; in the second embodiment, a radial-flow blower is used.

In addition, the side walls 5 and 6 are directly welded to the lower tubular component 14 in such a way that said lower tubular component defines the rear wall 8.

The mode of operation corresponds to that of the first embodiment, the only difference being that the air now flows to the fine-dust filter directly and no longer through the openings 9.

Figure 5:
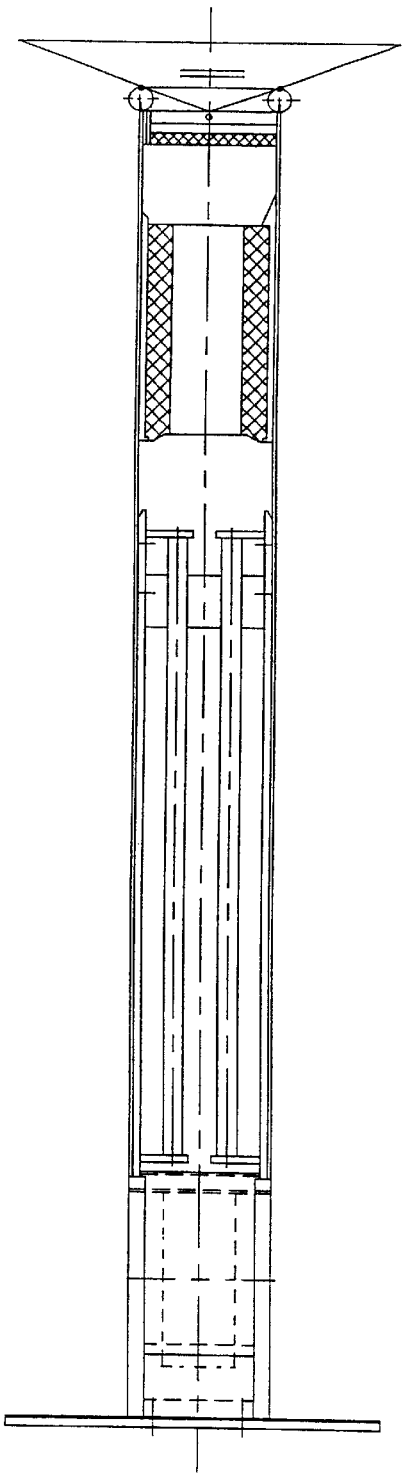
FIG. 5 shows the vertical section of a third embodiment.
Figure 6:
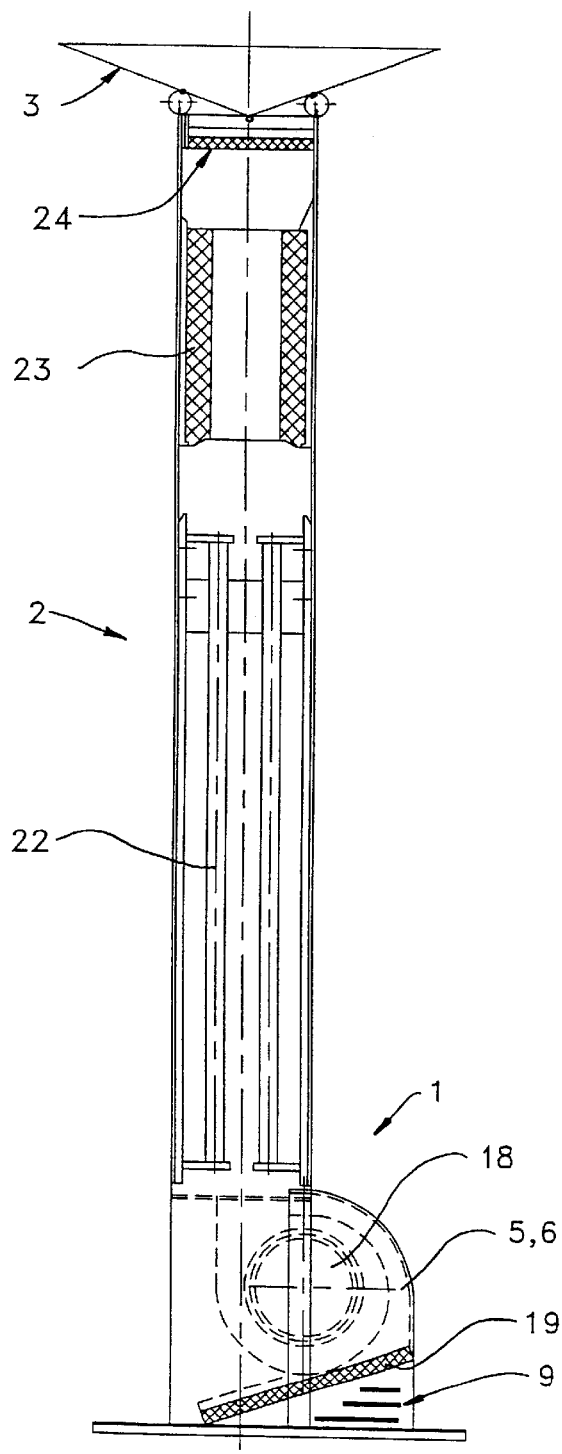
FIG. 6 shows the side view of a third embodiment, said view being partly in section.

FIGS. 5 and 6 show the third embodiment.

This third embodiment uses, like the second one, a radial-flow blower 18. The fine-dust filter 19 is located in the interior of the housing 1. Instead of one large opening, the sides are provided with a plurality of narrow slots 9. The mode of operation correponds to that of the first embodiment.

Further Advantages

Due to the large distance, approx. 1.80 m, between the opening 9 sucking in the ground air 25 and the discharge cone 3, it is guaranteed that the air discharged will first spread in the room and mix with the rest of the air in said room before it is sucked in again.

Hence, the formation of a short air circuit, viz. that the air discharged is directly sucked in again, is reliably avoided; such a short air circuit would have the consequence that, although the breathing air would be filtered directly adjacent the device, it would no longer be filtered at some distance therefrom.

The roughing filter protects the UV-C lamps and the main filter. This will facilitate maintenance. Whereas the roughing filter has to be replaced approximately every six months, it will suffice to replace the main filter every second year. (*)

(*) Due to the high lint content of the mull-bandage dressing material, it may be necessary to exchange the roughing filter every three months in operating rooms.

In view of the fact that the bacteria, viruses and microorganisms are destroyed before they can reach the main filter, they can neither reproduce in nor grow through said main filter.

The lamp holder 30 projects beyond the parting plane 16 of the upper and lower tubular members 15/16. The ends 31 of the lamp holder 30 are slightly bevelled. During assembly of the tubular components, the components can therefore be easily attached and guided. In addition, a small part of the UV-C lamps is also located above the parting plane 16. This serves to make the UV-C lamps easily accessible when the upper tubular member 15 has been removed so that they can be grasped by hand in case of replacement.

Advantageous Further Development

The discharge cone 3 receives in its cone a lamp 26. In accordance with a further development, this lamp can be an annular lamp. The device thus serves as a floor lamp and because it shines onto the ceiling it is particularly suitable as ceiling illuminator.

Reference numerals 27 and 28 indicate electric switches. These switches can also be implemented as controllers so that the brightness and the amount of air can be adjusted.

The unit is constructed such that it is capable of providing 180 m³ of absolutely clean air of uniform quality per hour.

The unit also fits into living room surroundings.

Although the noise level is the lowest noise level that can be achieved by technically sensible means, it has a value of approx. 60 db(A), the user, who suffers e.g. from hay fever, can reduce the filtering of the breathing air, i.e. the amount of air filtered, when he begins to feel better, whereby the noise level will be reduced still further. The noise level can be reduced to 46 db(A) in this way, the throughput of air being then 60 m³ per hour.

For keeping the noise emission low, an adjusting transformer is provided for controlling the fan.

For restricting not only the emission of noise but also the consumption of energy to a low value, the fan can be controlled by means of a frequency converter in accordance with a further development of the present invention.

The inner surface of the tube 2, especially the area illuminated by the UV-C lamps, can be metallized in accordance with a further development of the present invention. This has the effect that the radiation is less rapidly absorbed by the wall. It crosses the room several times. This has an advantageous influence on disinfection.

The device can be produced from metal as well as from plastic material. If it is produced from plastic material, the metallization will protect the plastic against the UV-C rays.

The welded joint can also be replaced by an adhesive connection.

If plastic material is used, the inner surface of the tube can be provided with an electrically conductive lacquer. This lacquer shunts the static charge generated by the flowing air to an earth connection.

In addition, the filters can be surrounded by a metallic net which is earthed.

What is claimed is:

1. A device for high-purity filtering and disinfecting air in an air stream, comprising:
   a housing,
   a fine-dust filter and a fan arranged on said housing for drawing an air stream into said housing through said fine-dust filter,
   an elongate air flow tube arranged on said housing and receiving at a first end thereof for flow therethrough said air stream from said housing,
   means inside said elongate air flow tube for disinfecting the air in said air stream by destroying microorganisms while simultaneously creating noxious fumes, a main filter for removing the microorganisms from the air stream and an activated carbon filter for removing the noxious fumes, all arranged in series inside said tube, and
   a discharge cone arranged at a second end of said air flow tube remote from said first end and adjacent said activated carbon filter to define an air outlet gap through which the air stream from said activated carbon filter directly exits the second end of said tube.

2. A device according to claim 1, wherein the housing the comprises
   a base plate,
   two side walls which are fastened to said base plate,
   a front wall connected to the side walls as well as the base plate, and
   a rear wall.

3. A device according to claim 2, wherein at least one of the walls has an air inlet opening.

4. A device according to claim 1, wherein the fan is secured in position with the aid of sound-insulating means.

5. A device according to claim 1, wherein the tube comprises a lower tubular component and an upper tubular component.

6. A device according to claim 5, wherein the lower tubular component has arranged therein the disinfecting means and the upper tubular component has arranged therein the main filter and the activated carbon filter.

7. A device according to claim 1, wherein the disinfecting means are UV-C lamps.

8. A device according to claim 1, wherein an inner surface of the tube is at least partly metallized.

9. A device according to claim 1, wherein an inner surface of the tube is provided with an electrically conductive lacquer.

10. A device according to claim 1, wherein at least one of said fine-dust filter, main filter and activated carbon filter is surrounded by a grounded metallic net.

11. A device according to claim 1, wherein an end of said tube has a plurality of balls arranged thereon, and the discharge cone is secured to said plurality of balls.

12. A device according to claim 1, wherein the discharge cone has arranged therein a lamp for illuminating the environment around the housing.

13. In combination, a floor lamp, and a filtering device, the filtering device being mounted to the floor lamp, the filtering device comprising:
    a housing,
    a fine-dust filter and a fan arranged on said housing for drawing an air stream into said housing through said fine-dust filter,
    an elongate tube arranged on said housing and receiving at a first end thereof for flow therethrough said air stream from said housing,
    means inside said elongate tube for disinfecting the air in said air stream by destroying microorganisms while simultaneously creating noxious fumes, a main filter for removing the microorganisms from the air stream and an activated carbon filter for removing the noxious fumes, all arranged in series inside said tube, and
    a discharge cone arranged at a second end of said tube remote from said first end to define an air outlet gap through which the air stream exits the second end of said tube.

14. The combination according to claim 13, wherein the floor lamp includes switches to adjust at least one of the light intensity emitted from the floor lamp and the amount of air flowing through the filter device.

* * * * *